United States Patent [19]
DeBellis

[11] Patent Number: 5,095,903
[45] Date of Patent: * Mar. 17, 1992

[54] EPI-CARDIAL ELECTRODE WITH AN INCORPORATED CARDIAC RADIO-FREQUENCY RECEIVER (C&R) FOR TEMPORARY HEART STIMULATION FROM THE OUTSIDE, PREARRANGED FOR PERMANENT STIMULATION

[75] Inventor: Ferruccio DeBellis, Rome, Italy

[73] Assignee: P.A. & M. S.p.A., Rome, Italy

[*] Notice: The portion of the term of this patent subsequent to May 7, 2008 has been disclaimed.

[21] Appl. No.: 397,411

[22] Filed: Sep. 14, 1989

[51] Int. Cl.5 .............................................. A61N 1/00
[52] U.S. Cl. ............................. 128/419 P; 128/419 R; 128/903
[58] Field of Search ........ 128/419 P, 419 PG, 419 R, 128/903

[56] References Cited

U.S. PATENT DOCUMENTS

| 4,187,854 | 2/1980 | Hepp et al. | 128/419 PG |
| 4,442,840 | 4/1984 | Wojciechowicz, Jr. | 128/419 P |
| 5,012,806 | 5/1991 | De Bellis | 128/419 P |

OTHER PUBLICATIONS

Preston, "A New Temp. Pacing Cath. with Improved Sensing and Safety Char.", American Heart Journal, vol. 88, No. 3, 9-1974, pp. 289-293.

Primary Examiner—Kyle L. Howell
Assistant Examiner—Kennedy J. Schaetzle
Attorney, Agent, or Firm—DeLio & Associates

[57] ABSTRACT

Equipment with an incorporated cardiac radio-frequency receiver (CPR) for temporary heart stimulation from the outside in case of open-heart operation, suitable to be left insitu to provide permanent stimulation if subsequently necessary. The equipment is formed of an electrode with epi-cardial stimulation tip, and a quick jack-type connection emerging from said cardiac radio-frequency receiver and suitable to rapidly and easily connect a permanent pacemaker.

5 Claims, 5 Drawing Sheets

EPI-CARDIAL ELECTRODE WITH AN INCORPORATED CARDIAC RADIO-FREQUENCY RECEIVER (C&R) FOR TEMPORARY HEART STIMULATION FROM THE OUTSIDE, PREARRANGED FOR PERMANENT STIMULATION

BACKGROUND OF THE INVENTION

The present invention relates to equipment with an incorporated cardiac radioreceiver (CRR) for temporary heart stimulation from the outside in case of open-heart operation, suitable to be left in situ to provide a permanent stimulation if subsequently necessary. The equipment is formed by an electrode with an epi-cardial stimulation tip, a cardiac radio-frequency receiver, and a quick jack-type connection emerging from said cardiac radio-frequency receiver and suitable for rapidly and easily connection to a permanent pacemaker.

As known, during open-heart surgical operations, the possibility of temporary artificial stimulation of the heart is always maintained; this is achieved by utilizing an electrode, the stimulation tip of which is temporarily fixed with a simple technique to the epimyocardium in a position corresponding to the left ventricle.

When the patient's thorax is closed, the free extremity of the electrode comes out through the thoracic wall and is connected to an external pacemaker.

After the prescribed period of rest and when artifical stimulation of the heart is no longer necessary, the electrode is extracted from the outside simply by pulling it. By doing so, whenever the patient's need for artificial stimulation becomes evident, it is necessary to perform another operation in order to implant a normal pacemaker.

The equipment described overcomes said drawback and offers more advantages.

According to the invention, the apparatus or equipment with an epi-cardial electrode is provided with an incorporated cardiac radio-frequency receiver for temporary stimulation in case of open-heart operation, and is provided with a device for connection to a permanent pacemaker.

After the necessary period of rest, the receiver is left permanently in situ.

Preferably, the device for connecting the electrode to a permanent pacemaker is essentially constituted of a quick jack-type connection, as described later. The equipment is implanted during the open-heart operation with the quick connection duly insulated, but the stimulating tip of the electrode is permanently fixed to the epimyocardium.

In this way the following objectives are attained:

a) The extremity of the electrode is not connected to an external pacemaker and does not cross the thoracic wall since the temporary stimulation is supplied, via the cardiac radio-frequency receiver, by an external radio-frequency transmitter (Personal pacemaker); since the extraction of the electrode is not required, risks of sepsis are avoided;

b) In the event of the patient needing artificial stimulation of the heart, subsequent to the prescribed period of rest, it is always possible to supply such stimulation in a timely way from the outside using the Personal pacemaker;

c) In the event of persistence of the need of artificial stimulation (indication of a need for a permanent pacemaker implantation) it is possible to implant a pacemaker with a simple superficial operation since only the pacemaker pocket has to be prepared; then the pacemaker can be connected to the cardiac radio-frequency receiver (CRR) using a stretch of electrode equipped with the plug for connecting it to the pin of the jack.

The advantages for the patient are:

Elimination of the electrode through the thoracic wall during the phase of temporary stimulation and reduction of the risks of sepsis.

Elimination of the always bothersome intervention of extracting the temporary electrode.

Possibility to maintain temporary stimulation from the outside for urgent needs.

Possibility to maintain temporary stimulation from the outside in case of urgent indication of need for permanent stimulation.

Great simplicity of the operation for the implantation of a permanent pacemaker when indicated.

Possibility to maintain the stimulation during the above-mentioned operation.

Possibility of periodic in-hospital checks of the pathological conditions of the patient (by means of the Personal pacemaker in the "laboratory" version).

Possibility of therapeutical interventions in the event the patient undergoes arrhythmic events; this therapy requires the use of the Personal pacemaker in the "anti-arrhythmic" version that is capable to carry out the following antiarrhythmic programs: overdrive; underdrive; coupled stimulation; burst stimulation.

Great psychological support to the patient and his family since the Personal pacemaker is easily operated by non-specialized persons who have been given the necessary instructions.

BRIEF DESCRIPTION OF THE DRAWINGS

The invention will now be described in more detail with reference to the attached figures where.

DETAILED DESCRIPTION OF THE INVENTION

Figure 1:
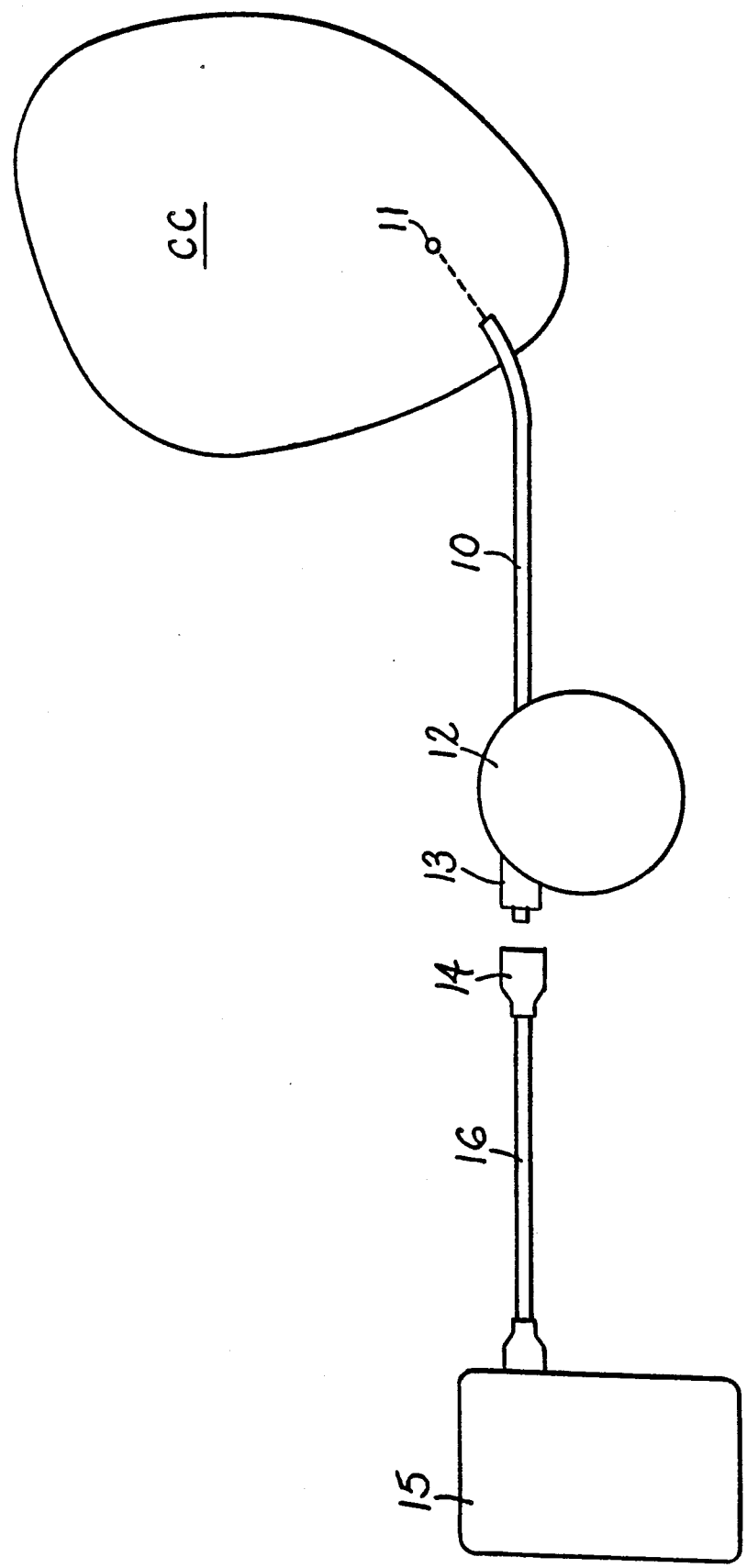
FIG. 1 is a schematic view of the equipment and of the heart that has to be stimulated.

From studying FIG. 1, the equipment is essentially formed of: an epi-cardial uni-polar electrode 11, one extremity of which stimulates the heart CC of the patient; a receiver of radio-frequency 12, clamped on the uni-polar electrode 10 without interrupting its mechanical continuity; a quick jack-type connection 13 for connecting the other extremity 14 of the uni-polar electrode 10.

Figure 2:
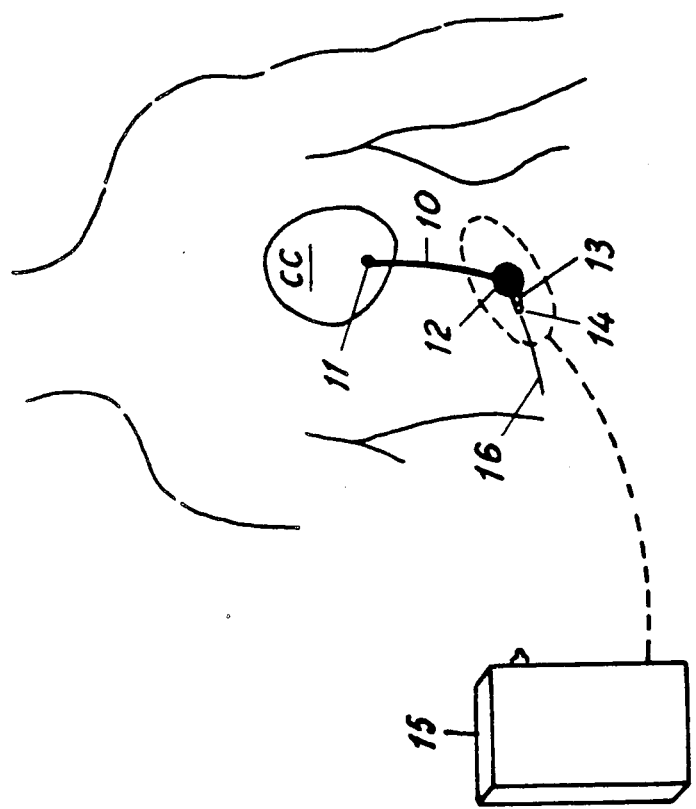
FIG. 2 is a schematic view of the equipment of FIG. 1 as implanted in a patient.

The equipment is permanently implanted during the operation by stitching the stimulation tip 11 of the electrode 10 on the epimyocardium of the heart CC of the patient; the radio-frequency receiver 12, constituted by a passive coil with a plate for the return signal closing through the patient's tissue, is located in a subcutaneous position (FIG. 2).

The cardiac stimulation that eventually will be required during or immediately after the operation is supplied by an external pacemaker (Personal pacemaker) transmitting the stimulation signals by radio-frequency to the radioreceiver 12. The return signal closes from the epi-cardial electrode onto the radioreceiver plate through the patient's tissue.

The equipment is then left in situ after the necessary period of rest has elapsed.

In case artificial stimulation of the patient's heart CC subsequently becomes necessary, immediate and temporary use of a Personal pacemaker can be made, or, in the event permanent stimulation is indicated, a permanent uni-polar pacemaker can easily and rapidly be implanted by simply opening the skin at the location of the radioreceiver 12 and connecting it to the permanent pacemaker 15 using a length or stretch of uni-polar electrode 16 connected to the extremity 18 by means of the quick connection 13.

Figure 4:
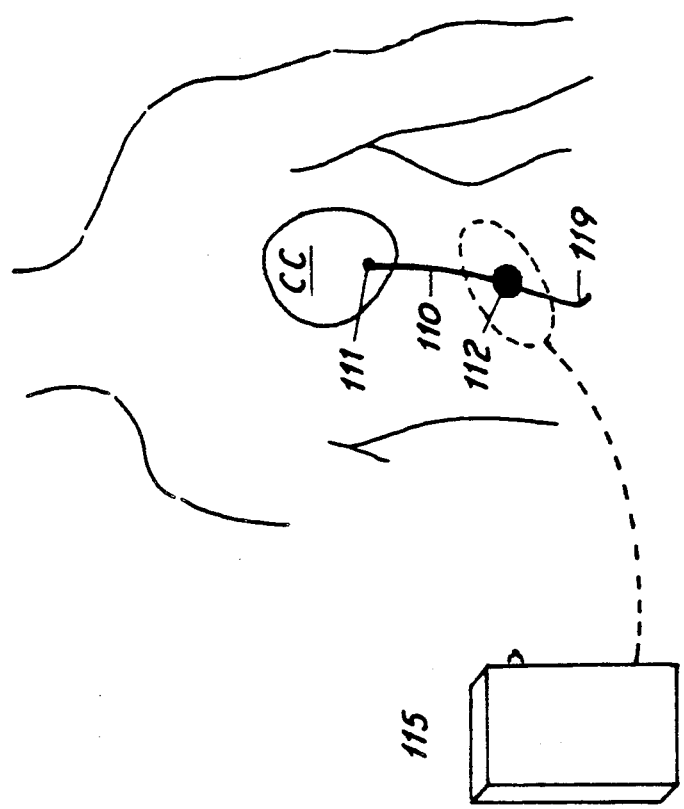
FIG. 4 is a view, similar to that of FIG. 2, relevant to the equipment of FIG. 3.
Figure 3:
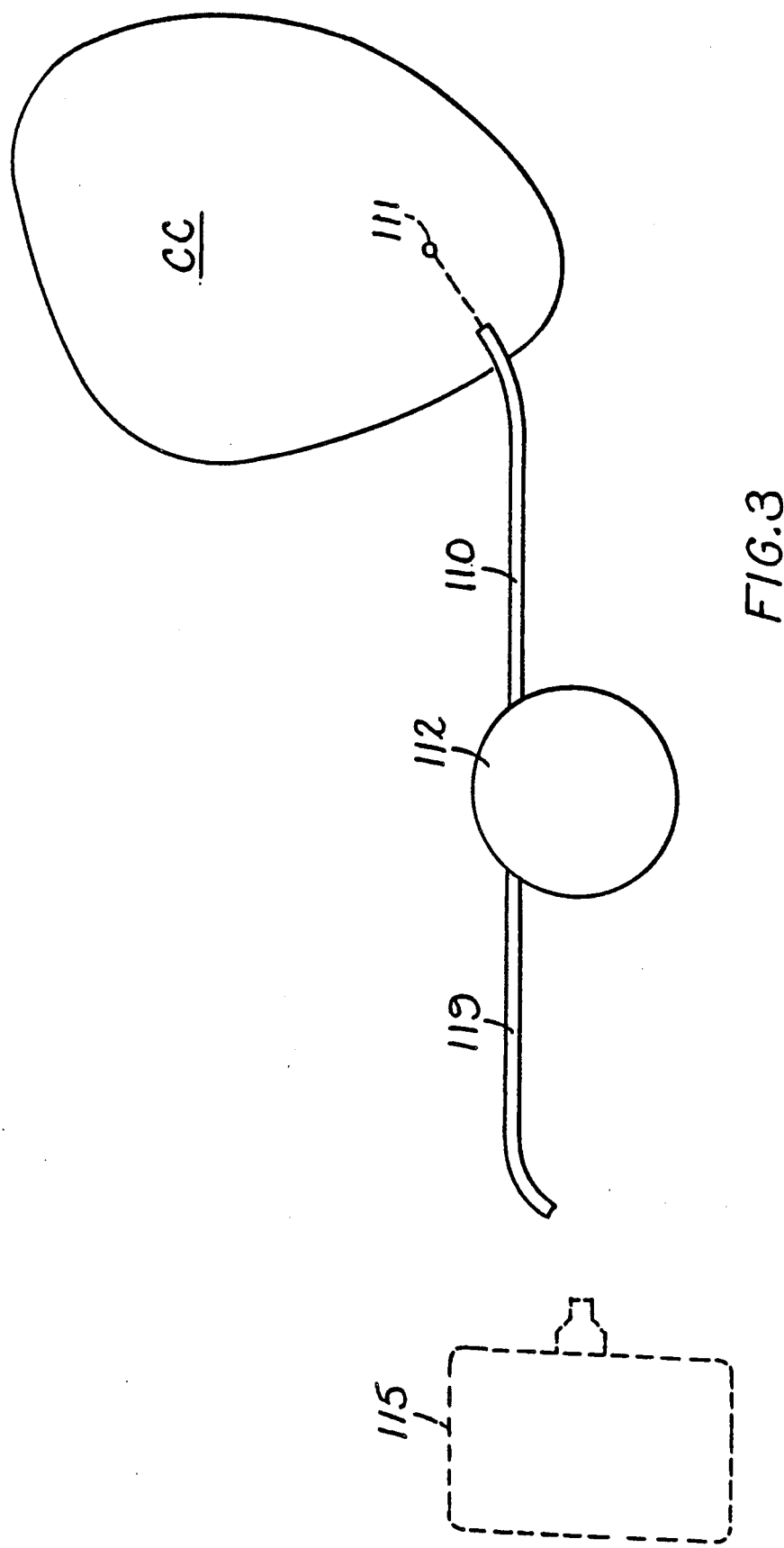
FIG. 3 is a view, similar to that of FIG. 1, of a second version of the invention.

As an alternative version of the invention, it is possible to utilize, instead of the quick jack-type connection 13 emerging from the radio-frequency receiver 12 as in FIG. 1, a well-insulated free length of uni-polar electrode of suitable length indicated as 119 in FIG. 3, emerging from the radio-receiver 112, that can easily be connected to the permanent uni-polar pacemaker 115 by a universal adaptor of a known type; the permanent pacemaker is implanted in a subcutaneous pocket previously prepared as normally done in permanent pacemaker implantations, as show in FIGS. 3 and 4. The return signal closes from the epimyocardical electrode onto the radio-frequency receiver through the patient's tissue. It may be noted that the equipment in this second version is identical to that of FIG. 1 as regards the uni-polar electrode, here indicated as 110, its stimulating tip indicated as 111 and the radioreceiver indicated as 112. The latter is clamped on the electrode 110 at a certain distance from its free extremity in order to leave a free length or "tail" of uni-polar electrode 110 to which the permanent pacemaker, as mentioned, can easily be connected.

Figure 5:
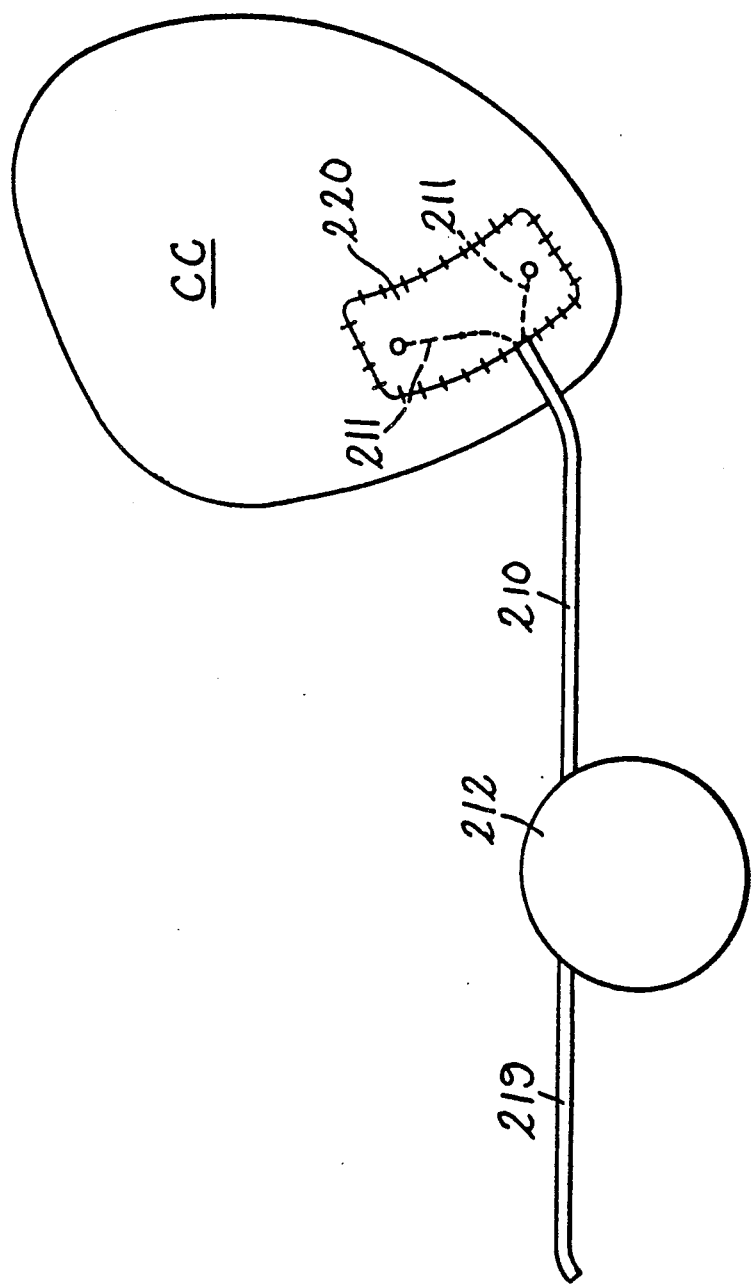
FIG. 5 is a view similar to that of FIG. 1 of the third version of the invention.
Figure 6:
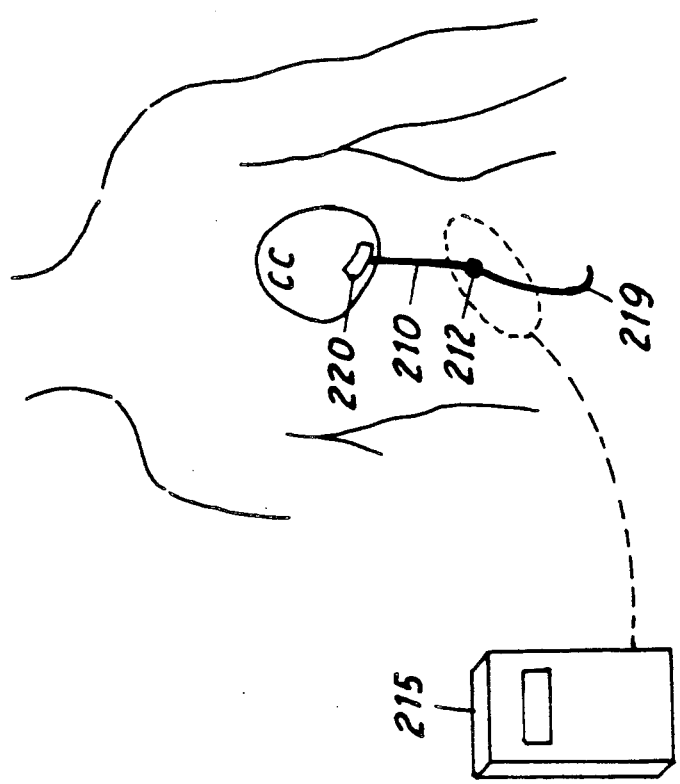
FIG. 6 is a view similar to that of FIG. 2 relevant to the equipment of FIG. 5.

One can see from FIG. 5, another alternative version of the invention using an epi-cardial bipolar electrode 211 formed by two stimulation tips screwed on the epimyocardium and positioned by means of a base 220 made of Tygon or other bio-compatible material stitched to the epimyocardium.

In this version the length of the electrode 210 is bipolar and the radio-frequency receiver 212 has the advanteage of miniaturization since its dimensions are no longer determined by the size of the signal return plate, which in this case is non-existent; moreover, the non-existence of the signal return plate avoids muscular contractions which are always possible due to accidental tipping of the radio-frequency receiver or to high current density.

The length of electrode 219 to connect the permanent pacemaker 215 can be indifferently uni-polar or bipolar, the permanent pacemaker being accordingly uni-polar or bipolar. The connection between the permanent pacemaker 215 and the electrode 219 is easily obtained by utilizing a universal adaptor of a known type, uni-polar or bipolar as appropriate. The advantages obtained with this third version of the invention are:

Avoiding contractions of muscles always possible in patients.

Complete miniaturization of the radio-frequency receiver.

It can be noted that the equipment in this third version of the invention is identical to that shown in FIG. 1 in its conceptual design, but utilizes a length of bipolar electrode 210, a bipolar epi-cardial electrode 211 with two stimulation tips screwed on the epimyocardium and positioned by means of a base 220 of bio-compatible material stitched to the heart, and a radio-frequency receiver 212, clamped on the conductors of the bipolar electrode 210, lacking the signal return plate and therefore very small.

I claim:

1. Apparatus for temporary heart stimulation during open-heart surgery by means of an external pacemaker transmitting radio frequency signals, and adapted to be left in situ to provide permanent stimulation if subsequently needed, comprising:

an electrode having an epi-cardial stimulation tip on one end;

a cardiac radio-frequency receiver capable of receiving radio-frequency stimulation signals clamped on said electrode; and connecting means, on an end opposite the epi-cardial stimulation tip, emerging from the radio-frequency receiver for easy and rapid connection of said electrode to a permanent pacemaker, the parts being arranged so that, at any time after the operation, said apparatus allows the supply of either an emergency radio-frequency stimulation or a permanent stimulation without the need for a new heart operation.

2. Apparatus for temporary heart stimulation during open-heart surgery by means of an external pacemaker transmitting radio frequency signals, and adapted to be left in situ to provide permanent stimulation if subsequently needed, comprising an electrode having an epi-cardial stimulation tip for stimulation of the heart; a cardiac radio-frequency receiver capable of receiving radio-frequency stimulation signals clamped on said electrode; and a connecting device for the easy and rapid connection of said electrode to a permanent pacemaker comprising a quick jack-type connection directly emerging from said radio-frequency receiver, the parts being arranged so that, at any time after the operation, said apparatus allows the supply of either an emergency radio-frequency stimulation or a permanent stimulation without the need for a new heart operation.

3. Apparatus for temporary heart stimulation during open-heart surgery by means of an external pacemaker transmitting radio frequency signals, and adapted to be left in situ to provide permanent stimulation if subsequently needed, comprising an electrode having an epi-cardial stimulation tip for stimulation of the heart; a cardiac radio-frequency receiver capable of receiving radio-frequency stimulation signals clamped on an intermediate portion of said electrode; and a connecting device for the easy and rapid connection of said electrode to a permanent pacemaker comprising an insulated free length of said electrode on the end opposite the epi-cardial stimulation tip emerging from said radio-frequency receiver, the parts being arranged so that, at any time after the operation, said apparatus allows the supply of either an emergency radio-frequency stimulation or a permanent stimulation without the need for a new heart operation.

4. The apparatus of claim 3 wherein the epi-cardial stimulation tip and the electrode between the stimulation tip and radio-frequency receiver are bipolar, and further including a base of bio-compatible material on which is positioned the bipolar epi-cardial stimulation tip, said base adapted to attach the stimulation tip to the heart.

5. The apparatus of claim 3 wherein the epi-cardial stimulation tip and the electrode between the epi-cardial stimulation tip and radio-frequency receiver are unipolar.

* * * * *

UNITED STATES PATENT AND TRADEMARK OFFICE
CERTIFICATE OF CORRECTION

PATENT NO. : 5,095,903

DATED : March 17, 1992

INVENTOR(S) : Ferruccio De Bellis

It is certified that error appears in the above-identified patent and that said Letters Patent is hereby corrected as shown below:

On the title page, and Col. 1, line 3:
"(C&R)" should read -- (CRR) --.

In the Abstract:

line 2, "(CPR)" should read --(CRR)--.

Column 1, line 38, please insert subheading -- SUMMARY OF THE INVENTION --.

Signed and Sealed this

Eighth Day of June, 1993

Attest:

MICHAEL K. KIRK

Attesting Officer

Acting Commissioner of Patents and Trademarks